US012638439B2

(12) United States Patent
Carromeu et al.

(10) Patent No.: US 12,638,439 B2
(45) Date of Patent: May 26, 2026

(54) METHOD OF USING HUMAN SPHEROIDS FOR DRUG DISCOVERY

(71) Applicant: AxoSim, Inc., New Orleans, LA (US)

(72) Inventors: Cassiano Carromeu, San Diego, CA (US); Robert T. Fremeau, Jr., Cambridge, MA (US)

(73) Assignee: AXOSIM, INC., New Orleans, LA (US)

( * ) Notice: Subject to any disclaimer, the term of this patent is extended or adjusted under 35 U.S.C. 154(b) by 0 days.

(21) Appl. No.: 18/169,999

(22) Filed: Feb. 16, 2023

(65) Prior Publication Data

US 2023/0228740 A1 Jul. 20, 2023

Related U.S. Application Data

(63) Continuation of application No. 16/778,283, filed on Jan. 31, 2020, now abandoned.

(60) Provisional application No. 62/800,430, filed on Feb. 2, 2019.

(51) Int. Cl.

| | |
|---|---|
| *G01N 33/50* | (2006.01) |
| *A61K 9/00* | (2006.01) |
| *A61K 31/137* | (2006.01) |
| *A61K 31/138* | (2006.01) |
| *A61K 31/19* | (2006.01) |
| *A61K 31/197* | (2006.01) |
| *A61K 31/343* | (2006.01) |
| *A61K 31/404* | (2006.01) |
| *A61K 31/4045* | (2006.01) |
| *A61K 31/416* | (2006.01) |
| *A61K 31/4178* | (2006.01) |
| *A61K 31/433* | (2006.01) |
| *A61K 31/4375* | (2006.01) |
| *A61K 31/439* | (2006.01) |
| *A61K 31/445* | (2006.01) |
| *A61K 31/4453* | (2006.01) |
| *A61K 31/4468* | (2006.01) |
| *A61K 31/4525* | (2006.01) |
| *A61K 31/454* | (2006.01) |
| *A61K 31/495* | (2006.01) |
| *A61K 31/496* | (2006.01) |
| *A61K 31/4985* | (2006.01) |
| *A61K 31/549* | (2006.01) |
| *A61K 31/5517* | (2006.01) |

(52) U.S. Cl.
CPC ....... *G01N 33/5058* (2013.01); *A61K 9/0019* (2013.01); *A61K 9/0053* (2013.01); *A61K 31/137* (2013.01); *A61K 31/138* (2013.01); *A61K 31/19* (2013.01); *A61K 31/197* (2013.01); *A61K 31/343* (2013.01); *A61K 31/404* (2013.01); *A61K 31/4045* (2013.01); *A61K 31/416* (2013.01); *A61K 31/4178* (2013.01); *A61K 31/433* (2013.01); *A61K 31/4375* (2013.01); *A61K 31/439* (2013.01); *A61K 31/445* (2013.01); *A61K 31/4453* (2013.01); *A61K 31/4468* (2013.01); *A61K 31/4525* (2013.01); *A61K 31/454* (2013.01); *A61K 31/495* (2013.01); *A61K 31/496* (2013.01); *A61K 31/4985* (2013.01); *A61K 31/549* (2013.01); *A61K 31/5517* (2013.01)

(58) Field of Classification Search
CPC .................................................. G01N 33/5058
See application file for complete search history.

(56) References Cited

U.S. PATENT DOCUMENTS

| | | | |
|---|---|---|---|
| 7,994,127 B2 | 8/2011 | Sur et al. | |
| 9,744,159 B2 | 8/2017 | During | |
| 11,193,159 B2 * | 12/2021 | Carromeu | ............ C12N 5/0671 |
| 2002/0040038 A1 | 4/2002 | Pratt | |
| 2009/0048234 A1 | 2/2009 | Volvovitz | |
| 2011/0059905 A1 | 3/2011 | Zesiewicz | |
| 2015/0119327 A1 | 4/2015 | Muotri et al. | |
| 2017/0182058 A1 | 6/2017 | Davis et al. | |
| 2019/0017097 A1 | 1/2019 | Carromeu | |

FOREIGN PATENT DOCUMENTS

| | | |
|---|---|---|
| WO | 2010020585 A1 | 2/2010 |
| WO | 2018053280 A1 | 3/2018 |
| WO | 2019023516 A1 | 1/2019 |
| WO | WO2019014603 A1 | 1/2019 |
| WO | 2020160470 A1 | 8/2020 |

OTHER PUBLICATIONS

Marchetto et al. Cell, Nov. 12, 2010, vol. 143, p. 527-539 (Year: 2010).*
Engle et al. Neuron, Nov. 21, 2018, vol. 100, p. 783-797 (Year: 2018).*
Sirenko et al. Toxicological Sciences, 2019, vol. 167, No. 1, p. 58-76 (Advance Access Publication Date: Aug. 31, 2018) (Year: 2019).*
Dong et al. eLife, 2018;7:e33417, 29 pages (Year: 2018).*
Crittenden et al. "Cell based assays on the FLIPR® Tetra System: Comparison of a novel FLIPR® calcium assay to other fluorescence based calcium flux assays", Molecular Devices, LLC, 2012, Poster, 1 page (Year: 2012).*

(Continued)

*Primary Examiner* — James D. Anderson
(74) *Attorney, Agent, or Firm* — Baker, Donelson, Bearman, Caldwell, & Berkowitz, PC

(57) ABSTRACT

The present invention discloses, in one embodiment, a method of using human induced pluripotent stem cells to generate three-dimensional human organ tissue for therapeutic drug toxicity and discovery•. In one embodiment, a high throughput microtiter plate is loaded with both wild type and Rett disease 3D spheroids and exposed to a drug library, and activity is measured and analyzed for disease rescue to wild type cell behavior.

20 Claims, 5 Drawing Sheets

(56) References Cited

OTHER PUBLICATIONS

Gika, A. D. et al. Trihexyphenidyl for acute life-threatening episodes due to a dystonic movement disorder in Rett syndrome. Movement Disorders, vol. 25, issue 3, pp. 385-389 (2010).

ISR for PCT/US2020/016209 mailed Jun. 24, 2020, 7 pages.

Langer, R. and Peppas, N. Chemical and Physical Structure of Polymers as Carriers for Controlled Release of Bioactive Agents: A Review. J. Macromol. Sci. Rev. Macromol. Chem., 23:61-126 (1983).

Lit et al, Salt Selection for Basic Drugs. Ivtt J Phann., 33, 201-217 (1986).

Mellios. N. et al. MeCP2-regulated miRNAs control early human neurogenesis through differential effects on ERK and AKT signaling. Mol Psychiatry 2018; 23: 1051-1065.

Percy, A. Rett Syndrome: Coming to Terms with Treatment. Advances in Neuroscience, vol. 2014, article ID 345270, 20 pages (2014).

Saglik, B. N. et al. Synthesis of new donepezil analogues and investigation of their effects on cholinesterase enzymes. Eur J Med Chem. 124:1026-1040 (2016).

WO for PCT/US2020/016209 mailed Jun. 24, 2020, 10 pages.

Costanzo, Paola, et al., "Design, synthesis, and evaluation of donepezil like compounds as AChE and BACE inhibitors", ACS Med Chem Lett 2016, pp. 470-475., (Mar. 28, 2016), 62 pages.

Green, Keith D., et al., "Multifunctional Donepezil Analogues as Cholinesterase and BACE1 Inhibitors", Molecules, 23, 3252; doi:10.3390/molecules23123252, (Dec. 8, 2018), 22 pages.

Vignoli et al. Epilepsy & Behavior, 2017, vol. 66, pp. 27-33 (Year: 2017).

Pintaudi et al. European Journal of Paediatric Neurology, 2015, vol. 19, pp. 446-452 (Year: 2015).

Ni, Mellions, "MeCP2-regulated miRNAs control early human neurogenesis through differential effects on ERK and AKT signaling", Molecular Psychiatry, vol. 23, No. 4, (Apr. 1, 2018), 1051-1065.

Yann, Ehinger, "Rett syndrome from bench to bedside: recent advances", F1000RESEARCH, vol. 7, (Jan. 1, 2018), 398.

Nicolas, Voituron, "The benzodiazepine Midazolam mitigates the breathing defects of Mecp2-deficient mice", Respiratory Physiology and Neurobiology, Elsevier, Amsterdam, NL, vol. 177, No. 1, (Feb. 4, 2011), 56-60.

Yildirim, Murat, "Third harmonic generation imaging of intact human cerebral organoids to assess key components pf early neurogenesis in Rett Syndrome (Conference Presentation)", Progress in biomedical optics and imaging, spie ¬ international society for optical engineering, bellingham, wa, us, vol. 10069, (Feb. 21, 2017).

Kadyan et al. Am. J. Phys. Med. Rehabil. 2003, vol. 82, No. 7, pp. 560-562 (Abstract Attached) (Year: 2003).

* cited by examiner

PRIMARY SCREENING USING THE SMART LIBRARY
MULTI-PARAMETRIC ANALYSIS

PRIMARY SCREENING USING THE SMART LIBRARY MULTI-PARAMETRIC ANALYSIS

Spontaneous Calcium Oscillations activity of Spheroids
High throughput kinetic calcium flux analysis using a FLIPR system
Spontaneous oscillations tracings shown

WT

RTT

Flumazenil

BIMU-8

100RFU

100SEC

METHOD OF USING HUMAN SPHEROIDS FOR DRUG DISCOVERY

CROSS-REFERENCE TO RELATED APPLICATIONS

This application is a continuation application of U.S. application Ser. No. 16/778,283, filed Jan. 31, 2020, which claims the benefit of the filing date of U.S. application Ser. No. 62/800,430, filed on Feb. 2, 2019, which is hereby incorporated by reference in its entirety for all purposes.

BACKGROUND

The use of mice and other animals as tools in biomedical research is well established. Their presence offers the ability to evaluate disease etiology and therapeutic profiling in a low cost, easy to maintain, rapidly reproducing mammalian model. For many years, attention has turned away from the forward genetics approach of studying spontaneous and chemically induced mouse models toward the reverse genetics approach to studying gene function via knockouts by genetic engineering. Through standard genetic engineering technologies, a tremendous amount of information has been gained with respect to gene function, pathways, and patho-physiology of disease by studying both constitutive and tissue-specific loss of function mutations. However, progress has been hampered by the costs associated with traditional genetic engineering, many of which are related to the time required to target embryonic stem (ES) cells, establish germ line transmission, and breed away from selectable markers. Furthermore, the lack of efficiency in ES cells from different inbred strains has limited the exploration of phenotypes on different genetic backgrounds. This limitation is an important point to consider when comparing disease models on a single inbred background to a heterogeneous patient population with possibly differential disease penetrance.

In developing and testing drugs for human use, animal trials provide extremely valuable information that is impossible to get from test tube or petri dish experiments alone. They provide how a drug is absorbed and spread around the body in a living animal and how it affects the targeted, and other, tissues. They also tell how the body processes and eliminates a drug, for most drugs, this is primarily done by the liver and kidneys. These studies help decide whether to progress the drug to human trials and, if so, what a reasonable starting dose for a human might be. However, because of species differences, something that is effective and safe in a non-human animal might not be so in a human.

Scientific journal publications on animal studies usually include a disclaimer along the lines of "this effect has only been demonstrated in animals and may not be replicated in humans". And with very good reason. A review looked at studies where medical interventions were tested on non-human animals and whether the results were replicated in human trials.

Most-cited non-human animal studies in prestigious scientific journals, such as Nature and Cell, only 37% were replicated in subsequent human randomized trials and 18% were contradicted in human trials. It is safe to assume that less-cited non-human animal studies in lesser journals would have an even lower strike rate. Another review found the treatment effect (benefit or harm) from six medical interventions carried out in humans and non-human animals was similar for only half the interventions. That is, the results of non-human animal and human trials disagreed half the time.

The mismatch between non-human animal trials and human trials can cause big problems. Developing a drug to the non-human animal trial phase is already incredibly expensive but taking it to human clinical trials adds enormous cost, often tens of millions of dollars. If a promising drug fails to impress in human trials, it can mean a lot of money, time and effort wasted.

But far more problematic is a drug that seems safe in non-human animal trials but turns out to be unsafe in humans. The consequences can be tragic. For instance, thalidomide (a drug to treat morning sickness) does not cause birth defects when given to pregnant rats and mice, but in humans it caused an international epidemic of birth defects, including severe limb malformations, in the 1950s and 1960s.

SUMMARY

The present disclosure provides for the use of a human model using tissue generated from human iPSC cell lines, thereby providing an alternative to animal models for drug safety and therapeutic testing. The cell lines are chosen that model the disease of interest for preclinical drug discovery and toxicity testing. The human tissue disease models of the present disclosure can be generated for most organs such as brain. heart, lung. kidney. liver, pancreas, spleen, skin, eve, muscle, and/or bone. The assays may use any one of the tissue models, or any combination thereof. In one embodiment, the model is a model for autism spectrum disorder and so the therapeutic compounds identified in the screen may be employed to prevent, inhibit or treat one or more symptoms of autism spectrum disorder or similar disorders, e.g., Rett syndrome. Autism spectrum disorder (ASD) is a neurological and developmental disorder that begins early in childhood and lasts throughout a person's life. It affects how a person acts and interacts with others, communicates, and learns. Therefore, a drug screening assay having a variety of different tissues may identify one or more compounds that are beneficial in treating one or more symptoms in one or more organ or tissues of patient with ASD.

For example, Rett syndrome affects numerous organ systems as it is characterized by neurological and developmental symptoms including but not limited to delayed growth, loss of normal movement and coordination, loss of communication abilities, abnormal hand and eye movements, breathing problems, cognitive disabilities, seizures, scoliosis, irregular heartbeat, and sleep disturbances. Thus, a drug screening assay having a variety of different tissues may identify one or more compounds that are beneficial in treating one or more symptoms in one or more organ or tissues of a Rett syndrome patient.

In one embodiment, the method provides an induced Pluripotent Stem Cell (iPSc) generated human disease tissue model for the testing and discovery of therapeutic drug compounds.

In one embodiment, the method provides an iPSC generated human tissue model for the testing and discovery of therapeutic drug compounds that has a 3-dimensional structure, e.g., a spheroid or three-dimensional spheroid form factor.

In one embodiment, the method provides an iPSC generated human tissue model for the testing and discovery of therapeutic drug compounds that has a 3-dimensional structure and is formatted into a high throughput array, e.g., high throughout microtiter array.

In one embodiment, the method provides an iPSC generated human tissue model for the testing and discovery of therapeutic drug compounds that has a 3-dimensional structure and can generate functional information about the tissue response, e.g., in disease versus control tissues, when exposed to therapeutic compounds.

In one embodiment, the method provides an iPSC generated human tissue model for the testing and discovery of therapeutic compounds that has a 3-dimensional structure that can replace the use of non-human animals in preclinical and clinical testing.

In one embodiment, the disclosure provides an optical assay, e.g., a functional FLIPR assay or high content high magnification optical microscopy, of 3D human cell spheroids e.g., mixed population human cell neuron spheroids.

In one embodiment, prior to testing, spheroids are cultured for 6 to 14 weeks, e.g., to induce robust synchronized synaptic networks to mimic mature human like brain functionality. Those mixed population of spheroids fired predictably and consistently for long periods of time. In one embodiment, the disclosure provides a high throughput optical assay of a mixed population of human cell 3D spheroids utilizing FLIPR and calcium uptake fluorescence oscillations. The oscillations could be modulated with chemical compounds, and oscillatory firing can be altered with agonist or antagonists. In one embodiment, the cells are from a patient with Rett syndrome or cells that are a model of Rett syndrome.

In one embodiment, the disclosure provides an optical method to detect the effect of one or more compounds on spheroids, e.g., from cells of a Rett syndrome patient or a model of Rett syndrome. The method includes contacting a tissue culture plate, e.g., a plate having wells, comprising one or more spheroids of human cells, e.g., from cells of a Rett syndrome patient or a model of Rett syndrome, spheroids of, for instance, uniform diameter and one or more test compounds; and optically detecting the amount or change in oscillations in the spheroids. In one embodiment, the plate is a multi-well plate. In one embodiment, the spheroids are further contacted with a fluorescent molecule useful to detect calcium, and the amount or change in fluorescence over time is detected. In one embodiment, the amount or change in fluorescence is detected via a quantity of peaks of fluorescence, an amplitude of one or more of the peaks, peak spacing between one or more of the peaks, a width of one or more peaks, or any combination thereof. In one embodiment, the spheroids comprise neurons. In one embodiment, the spheroids comprise neurons and astrocytes. In one embodiment, the spheroids comprise heart, liver, kidney, pancreas, lung, endothelial or epithelial cells. In one embodiment, the spheroids comprise microglial cells or oligodendrocytes. In one embodiment, the spheroids comprise pericytes and endothelial cells. hi one embodiment, the spheroids comprise endothelial cells, microglial cells, neurons, oligodendrocytic cells, or any combination thereof. In one embodiment, the cells are differentiated cells. In one embodiment, the progenitor cells are progenitors of neurons, astrocytes, heart cells, liver cells, kidney cells, pancreas cells, lung cells, endothelial cells, or epithelial cells. In one embodiment, the one or more spheroids have a diameter of about 500 to about 600 microns. In one embodiment, the one or more spheroids have a diameter of about 450 to about 500 microns. In one embodiment, the one or more spheroids are cultured for at least 4 to 6 weeks before contacting with the one or more test compounds. In one embodiment, the fluorescent molecule comprises Calcium 3, Calcium 4, Calcium 5, Calcium 6, Fluo 3, or Fluo4, or a combination thereof. In one embodiment, the one or more spheroids are further contacted with a cell membrane impermeant quencher. In one embodiment, the amount of change in fluorescence is compared to the fluorescence with one or more spheroids and the fluorescent molecule but no test compound. In one embodiment, in a multi-well plate each well has one spheroid.

Also provided is a multi-well plate comprising one or more mixed human cell spheroids, e.g., from cells of a Rett syndrome patient or a model of Rett syndrome, per well. In one embodiment, the spheroids comprise neurons and astrocytes. In one embodiment, the spheroids comprise heart, liver, kidney, pancreas, lung, endothelial or epithelial cells. In one embodiment, the spheroids comprise microglial cells or oligodendrocytes. In one embodiment, the spheroids comprise pericytes and endothelial cells. Tn one embodiment, the spheroids comprise endothelial cells, microglial cells, neurons, oligodendrocytic cells, or any combination thereof. In one embodiment, the spheroids comprise progenitors of neurons, astrocytes, heart cells, liver cells, kidney cells, pancreas cells, lung cells, endothelial cells, or epithelial cells.

DETAILED DESCRIPTION

Definitions

Figure 1:
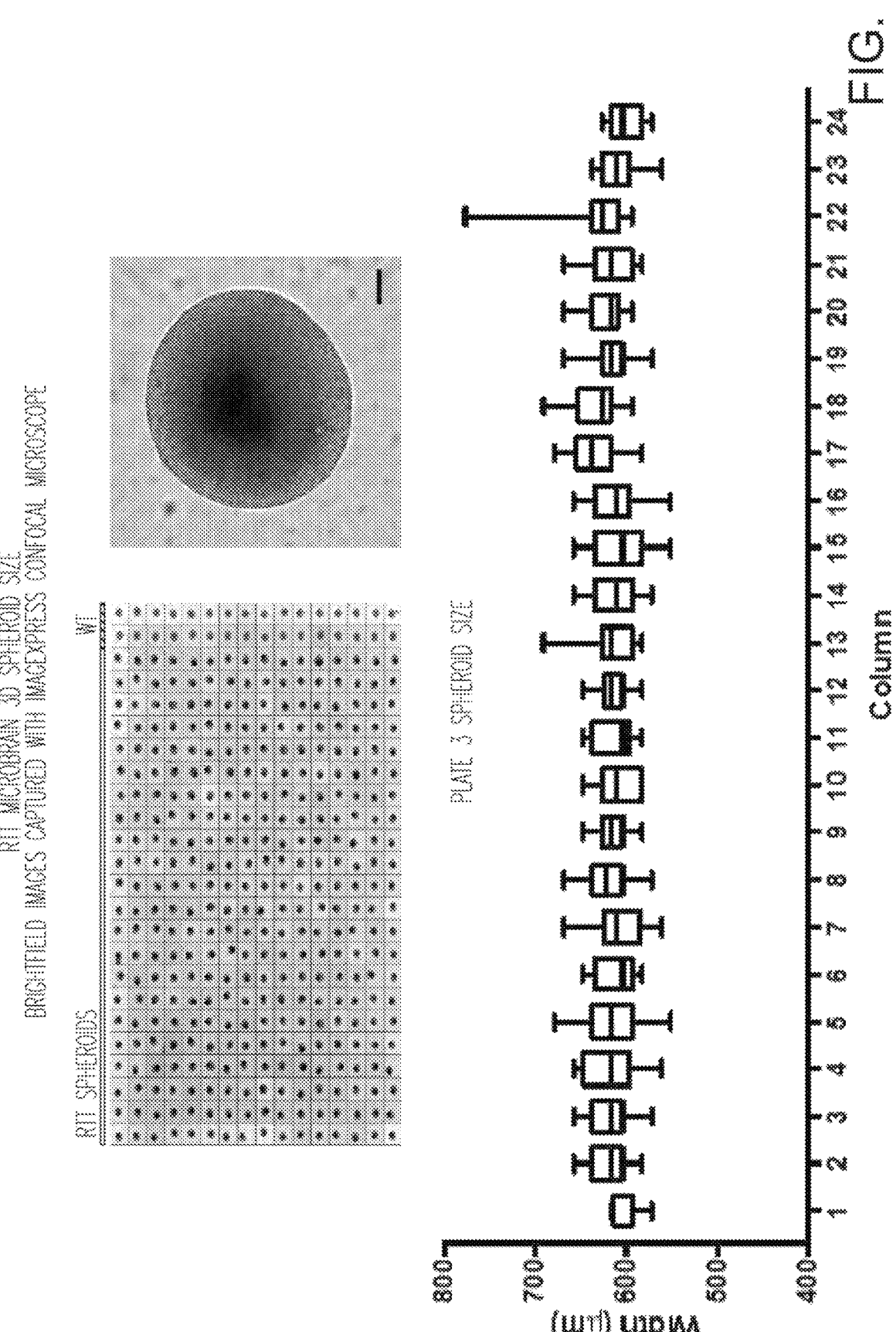
FIG. 1 shows microscopic images of cortical brain spheroids in a high throughput format, a single well and the spheroid size distribution.

In describing the invention, the following terminology will be used in accordance with the definitions set forth below.

The articles "a" and "an" are used herein to refer to one or to more than one (i.e., to at least one) of the grammatical object of the article. By way of example, "an element" means one or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%. The term "about", when referring to a numerical value or range, allows for a degree of variability in the value or range, for example, within 10%, or within 5% of a stated value or of a stated limit of a range.

The terms "disease" and "disorder" and "syndrome" are used 30 interchangeably.

The expression "effective amount", when used to describe therapy to an individual suffering from a disorder, refers to the amount of a compound or composition that is effective to prevent or inhibit or otherwise treat one or more symptoms of a disease or disorder.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

The administration of a composition may be for either a "prophylactic" or "therapeutic" purpose. When provided prophylactically, the compositions are provided before any symptom or clinical sign of a disease becomes manifest. The prophylactic administration of the composition serves to prevent or attenuate any subsequent symptom or clinical sign. When provided therapeutically, the compositions are provided upon the detection of a symptom or clinical sign of disease.

Thus, a composition may be provided either before the onset of disease or a symptom (so as to prevent or attenuate a symptom) or after the initiation of symptoms or clinical signs of disease.

A composition is said to be "pharmacologically acceptable" if its administration can be tolerated by a recipient mammal, such as a human. Such an agent is said to be administered in a "therapeutically effective amount" if the amount administered is physiologically significant.

The "protection" provided need not be absolute, i.e., need not be totally prevented or eradicated, if there is a statistically significant improvement compared with a control population or set of mammals. Protection may be limited to mitigating the severity or rapidity of onset of symptoms or clinical signs of the disease.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder.

Similarly, as used herein, an "effective amount" or a "therapeutically effective amount" of a compound described herein refers to an amount of the compound that alleviates, in whole or in part, symptoms associated with the disorder or condition, or halts or slows further progression or worsening of those symptoms or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH4+ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydrox-yethanesulfonic, p-toluenesulfonic, sulfanilic, cyclohexylaminosulfonic, stearic, alginic, P-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, NX-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Lit et al., Salt Selection for Basic Drugs (1986), Intl. Pharm., 33, 201-217, incorporated by reference herein.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

Exemplary Assay Methods

In one embodiment, the present disclosure provides human induced pluripotent stem cells iPScs that are subsequently differentiated into human cortical neurons comprising neurons and astrocytes in approximately a 50:50 ratio. The ratio can be adjusted on a case by case basis depending on the particular disease of interest from 1 to 99% either neurons or astrocytes. The 3D spheroids are comprised of approximately 50:50 neurons to astrocytes ratio +1-10%. The methods of differentiating and forming 3 dimensional spheroids and functional testing with FLIPR optical techniques is described in copending patent application No. 62/532667. In the examples in this invention we use a disease model cell line which are known to carry genes responsible for Rett syndrome.

Rett (RTT) syndrome is a unique postnatal neurological disorder that is first recognized in infancy and seen almost always in girls but can be rarely seen in boys. Rett syndrome has been most often misdiagnosed as autism, cerebral palsy, or non-specific developmental delay Rett syndrome is caused by mutations on the X chromosome on a gene called MECP2. There are more than 200 different mutations found on the MECP2 gene. Most of these mutations are found in eight different "hot spots." Rett syndrome strikes all racial and ethnic groups and occurs worldwide in 1 of every 10,000 female births. Rett syndrome is a postnatal neurological disorder. It is not a degenerative disorder. Rett syndrome causes problems in brain function that are responsible for cognitive, sensory, emotional, motor and autonomic function. These can include learning, speech, sensory sensations, mood, movement, breathing, cardiac function, and even chewing, swallowing, and digestion.

Rett syndrome symptoms appear after an early period of apparently normal or near normal development until six to eighteen months of life, when there is a slowing down or stagnation of skills. A period of regression then follows when she loses communication skills and purposeful use of her hands. Soon, stereotyped hand movements such as handwashing, gait disturbances, and slowing of the normal rate of head growth become apparent. Other problems may include seizures and disorganized breathing patterns while she is awake. In the early years, there may be a period of isolation or withdrawal when she is irritable and cries inconsolably. Over time, motor problems may increase, but in general, irritability lessens, and eye contact and communication improve. Rett syndrome is confirmed with a simple blood test to identify the MECP2 mutation. However, since the MECP2 mutation is also seen in other disorders, the presence of the MECP2 mutation in itself is not enough for the diagnosis of Rett syndrome. Diagnosis requires either the presence of the mutation (a molecular diagnosis) or confirmation of the diagnostic criteria (a clinical diagnosis, based on signs and symptoms that you can observe) or both.

Rett syndrome can present with a wide range of disability ranging from mild to severe. The course and severity of Rett syndrome is determined by the location, type and severity of the mutation and X-inactivation. Therefore, two girls of the same age with the same mutation can appear quite different.

In the present disclosure both Wild Type (WT) and Rett Disease (RTT) cortical brain human tissue spheroids were prepared for the purpose of high throughput screening to identify therapeutic compounds that can modulate the brain activity in an attempt to revert or rescue the disease state back to near normal activity or homeostasis. For example, the cell lines employed (control or "WT" and disease "RTT") may be from a family without and with the Rett disease phenotype.

The method disclosed herein may, in one embodiment, include manufacturing 3D spheroids in 384 well round bottom microtiter plates, see, e.g. U.S. patent application No. 62/532,667, the disclosure of which is incorporated herein. Once the spheroids have been produced and subsequently aged to greater than 6 weeks of maturation it is possible at that time to start testing potential therapeutic compounds. In the present disclosure, 6 to 14 weeks of maturation is a maturation range for testing, e.g., 8 to 10 weeks of maturation.

Referring to FIG. 1, this image and the left shows a 384 well microtiter plated where each well has been loaded with a human tissue microsphere that is approximately 600 microns in diameter and each sphere has approximately 10,000 cells. The microtiter well number may range from 28 to 1536 wells per plate or 96 and 384 wells. The number of cells that form each spheroid may range from 2500 to 50000 cells or 5000 to 15000. The right-hand image shows the uniformity on a microsphere in a single well. Uniformity is very important in this invention in order to have very reproduceable results and limit variability from well to well and plate to plate. The bottom image is a plot showing the average spheroid size across a row of microliter wells. The spheroid size may range from 100 microns to 5 millimeters or 400 to 800 microns.

Figure 2:
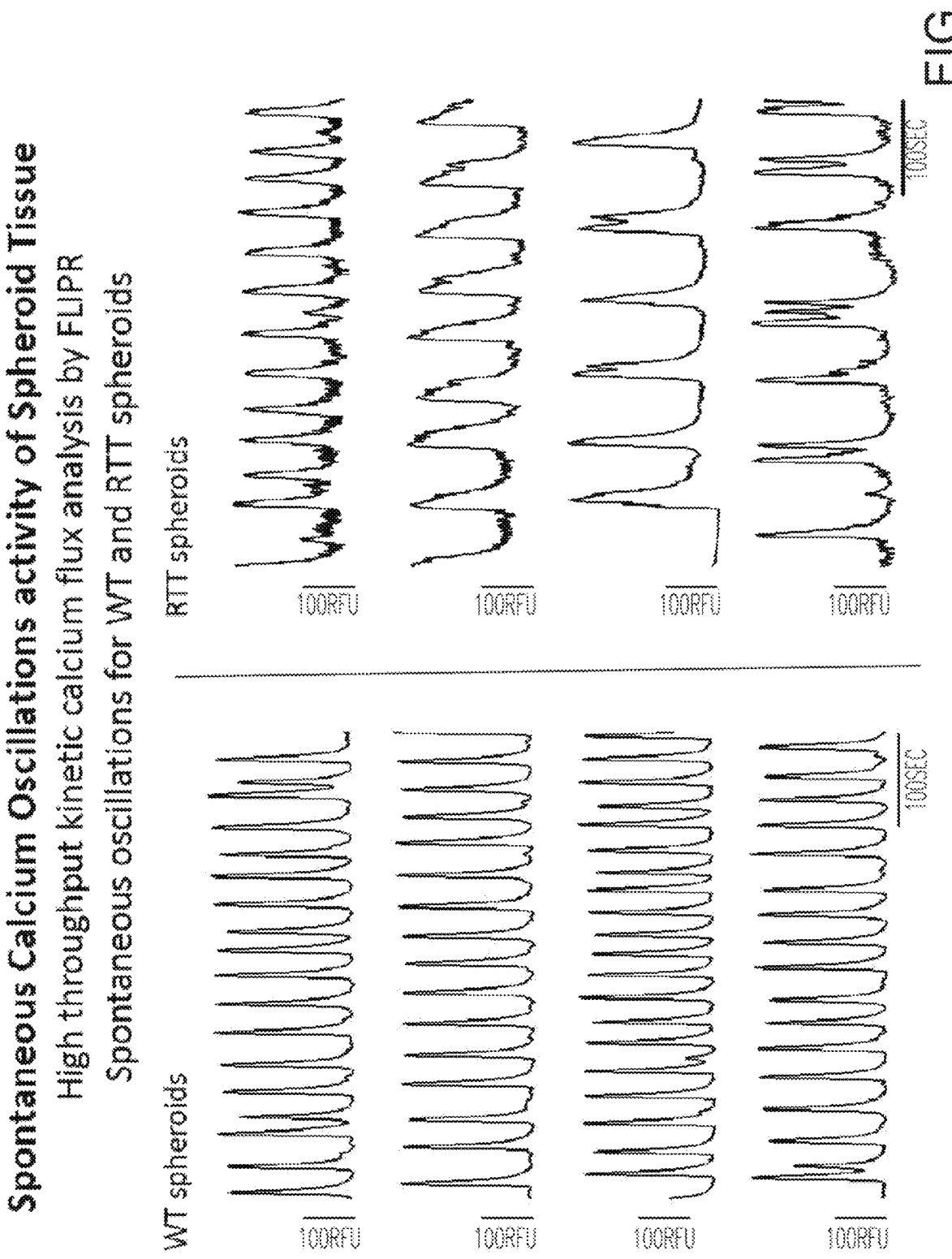
FIG. 2 shows calcium oscillation activity of both Wild Type (WT) and Rett (RTT) spheroids captured from different wells.

Referring to FIG. 2, this figure shows examples of both WT and RTT spheroids from randomly selected wells prior to any therapeutic drug exposure. The oscillations being measured are from calcium flux moving into and out of the cells at ambient conditions. The oscillations are spontaneous and not generated by an external source. The measurements are conducted in real time and the data captured by using a technique called FLIPR that is well known in the prior art. As can be seen in the image the WT spheroids have a very regular periodic peak intensity from selected random wells. However, the RTT disease spheroid model on the right is very erratic and somewhat unpredictable. This observation coincides with the erratic behavior seen in patients with the Rett phenotype and described in the aforementioned description. When analyzing the data, it is important to understand that multiple factors contribute to the signal being recorded by the FLIPR software. Therefore, in the present disclosure 7 parameters are recorded to determine if the data generated from the spheroid is meaningful. The parameters measured are, e.g., peak count, peak width, average peak spacing, peak spacing standard deviation, peak decay time, peak rise time, and/or peak amplitude. By comparing the WT spheroid multiparameter data to the RTT data before and after drug exposure one can determine if a potential therapeutic candidate can have efficacy in rescuing the disease state back to the WT normal state.

In the present disclosure, the SMART library that contained 298 compounds was used on both WT and RTT matured spheroids over several weeks and the FLIPR data collected and analyzed for potential therapeutic efficacy. The SMART (Selected Molecular Agents for Rett Therapy) library of compounds is well vetted by modern day bioinformatics methods, tightly focused on Rett syndrome and its biological causes. The library is currently housed at the University of Illinois-Chicago. The Rettsyndrome.org Science Advisory Board has also recommended a number of compounds that have been either purchased or prepared and are now included in the library. With the goals in mind to save both time and resources and accelerate drug discovery for Rett syndrome, the compounds in the SMART library are readily available to investigators working on Rett syndrome research.

Figure 3:
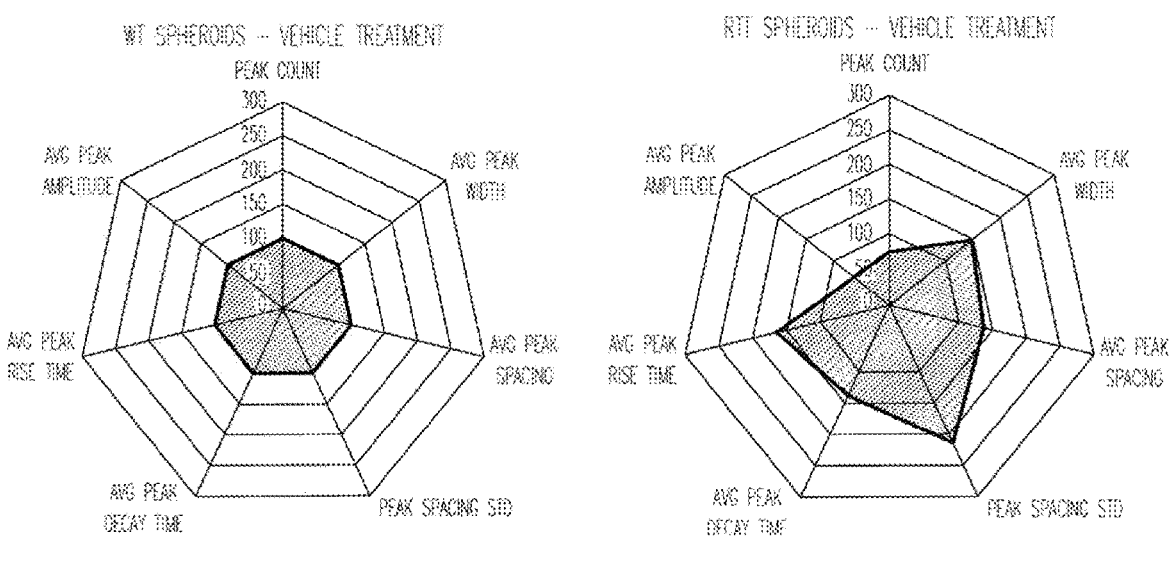
FIG. 3 shows multi parametric plots of spheroid calcium oscillation activity of WT, and WIT spheroids before and after BIMU-8 and Flumazenil drug exposure.
Figure 3:
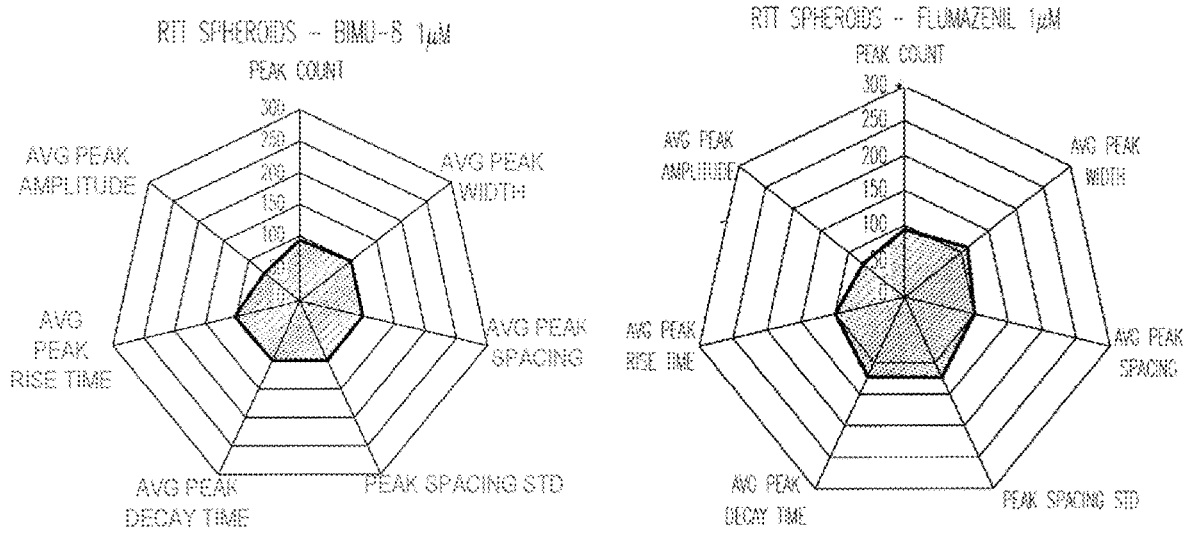

Referring to FIG. 3, this shows the results of WT, and RETT spheroids that are exposed to a vehicle which has no effect on the spheroids the top 2 images. in the figure and on the bottom RTT spheroids that have been exposed to a 1 micro molar dose of BIMU-8 and Flumazenil from the SMART library. As can be seen in FIG. 3, both BIMU-8 and Flumazenil had a significant effect on reversing or rescuing the RTT disease state to a near normal multivariant graph as shown in the upper left had corner of FIG. 3, that was generated for WT spheroids.

Figure 4:
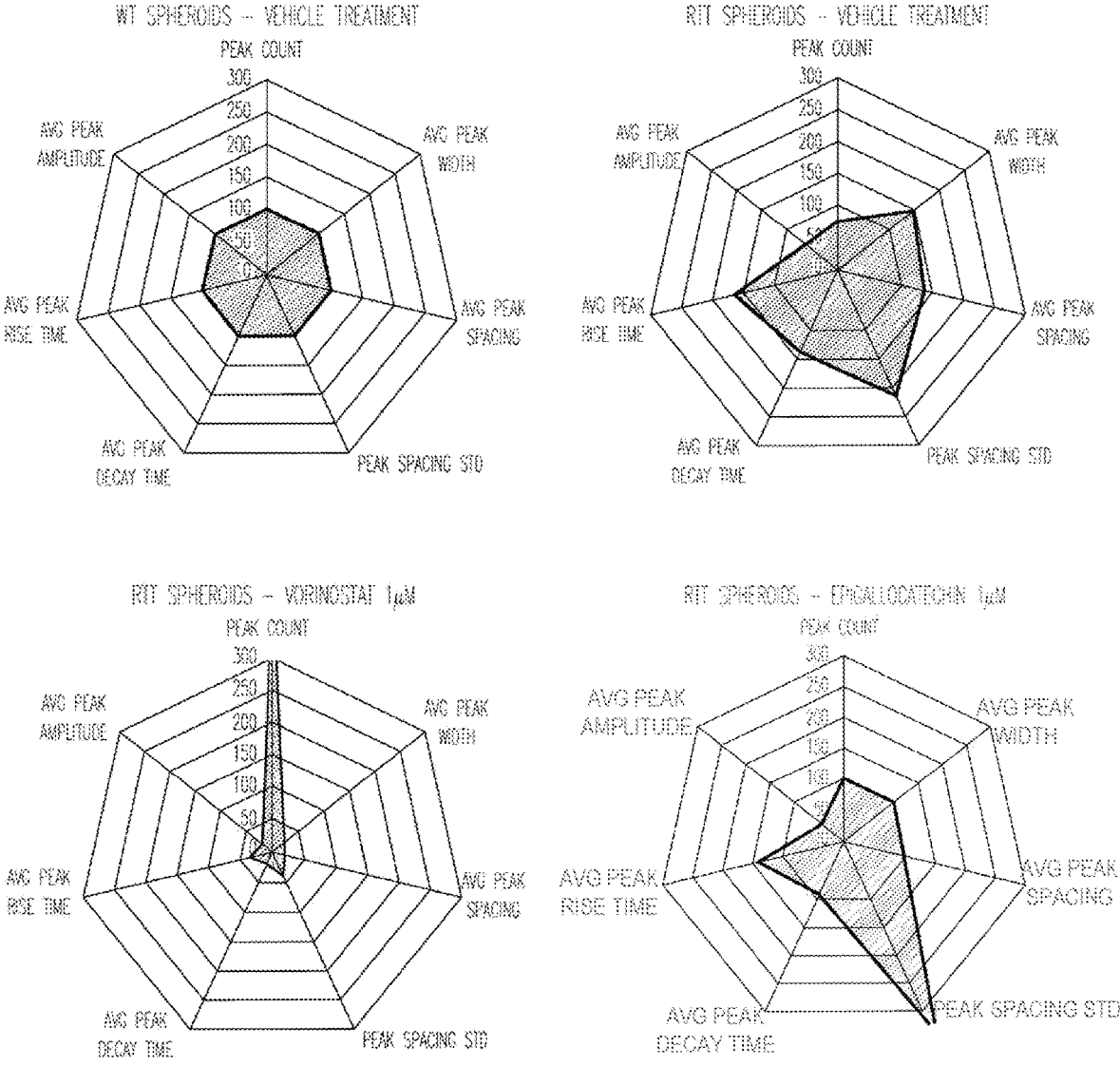
FIG. 4 shows a multi parametric plots of spheroid calcium oscillation activity of WT and RTT spheroids before and after exposure to vorinostat and epigallocatechin.

This is stark contrast to FIG. 4, where WT and RTT exposure to 1 micro molar concentration of Vorinostat and Epigallocatechin showed no effect to rescue or reverse the spontaneous calcium oscillations in the spheroids (bottom multivariant plots). In fact, it the drugs made the condition worse.

Figure 5:
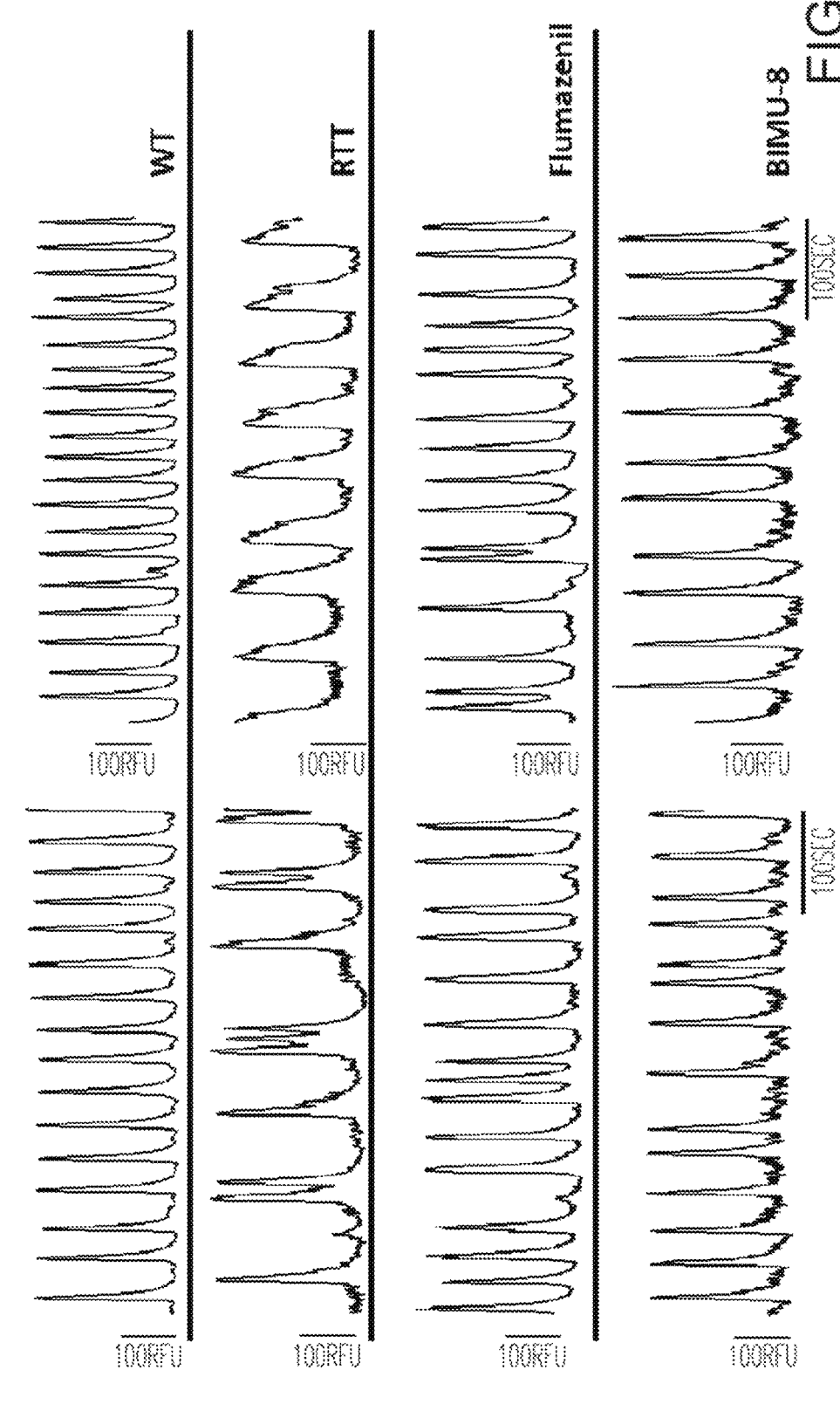
FIG. 5 shows calcium oscillation activity of WT and RTT spheroids after exposure to flumazenil and BIMU-8 drug molecules demonstrating rescuing the oscillation activity back to WT normal behavior.

Referring to FIG. 5, this shows spontaneous calcium peaks captured and plotted from random microtiter wells of WT, RTT and RTT spheroids exposed to Flumazenil and BIMU-8 over a 2-week exposure time. As can be seen from the bottom two images the drug candidates nearly rescued the WT state of cell spheroid peak frequency and amplitude behavior. Based on these results and the multivariant analysis the assay identified approximately 10% of the SMART library as therapeutic candidates and possible drugs for a preclinical or clinical trial. Rett syndrome therapeutics of interest from the SMART library include, but are not limited to, Acetazolamide, Atomoxetine (Tomoxetine), Benzhexol Hydrochloride, BIMU-8, Eletriptan HBr Salt, Iloperidone, Trazodone (Beneficat), Valproate DPA, Baclofen, Benzydiamine Hydrochloride, Bromoindirubin-3-oxime, Biperiden, Citalopram, Clebopride Mal ate, Donepezil, Flumazenil, Hydroxyzine Dichloride, IDRA-21, Ondansetron, Paroxetine, Pinmavanserin, Pirlindole Mesylate, Selegiline Hydrochloride, and Vinpocetine. These potential therapeutics as well and their derivatives are good candidates for the treatment of Rett syndrome. Compounds that are effective for Rett syndrome may also be effective for other autism conditions.

Spheroids, such as those formed from two or more different cell types, may be prepared using any suitable medium, optionally including one or more different growth factors, and any suitable conditions. For example, spheroids 13 formed from neurons and astrocytes may be prepared using, in one embodiment, one or more of the following media and/or conditions: BrainPhys™ Neuronal Medium (StemCell Tech) supplemented 1x with SM I Neuronal Supplement (BrainPhys.' Neuronal Medium and SM1 Kit (cat. # 05792; StemCell Technologies), 20 nglinL BDNF (cat. # 78005; StemCell Technologies), 20 ng/mL GDNF (cat. # 78058; StemCell Technologies) and penicillin/strep- tomycin (cat. # SV30010; GE Healthcare Life Sciences). The cells are maintained at 37° C. in an incubator with 5% CO2 and high humidity.

The present subject matter allows for multiple approaches for analyzing the effects of one or more compounds on spheroids, comprising contacting a plate, e.g., a multi-well plate having wells, comprising one or more spheroids of human cells of uniform diameter, a fluorescent molecule useful to detect calcium, and one or more test compounds; and optically detecting the amount or change in fluorescence over time, e.g., in each well. In various examples, the method detects the amount or change in fluorescence via a quantity of peaks of fluorescence, an amplitude of one or more of the peaks, peak spacing between one or more of the peaks, a width of one or more peaks, or any combination thereof. In various examples, the foregoing methods may include wherein the spheroids comprise neurons or wherein the spheroids comprise neurons and astrocytes, or wherein the spheroids comprise heart, liver, kidney, pancreas, lung, endothelial or epithelial cells, or wherein the spheroids comprise cancer cells. In various of the preceding examples, the spheroids may comprise a plurality of different cell types. In the foregoing examples, some examples include wherein the cells are derived from human iPSCs. In some examples, the cells are differentiated cells. In some examples, the cells are progenitor cells. In some examples using progenitor cells, the progenitor cells are progenitors of neurons, astrocytes, heart cells, liver cells, kidney cells, pancreas cells, lung cells, endothelial cells, or epithelial cells.

In various of the foregoing methods, the spheroids may have a diameter of about 500 to about 600 microns or a diameter of about 450 to about 500 microns. In various of the foregoing methods, the spheroids may have been in culture for at least 6 weeks. In various of the foregoing methods, including a fluorescent molecule, the molecule comprises Calcium 3, Calcium 4, Calcium 5, Calcium 6, Fluo 3, or Fluo4.

In one embodiment, an optical assay is provided, e.g., a functional FLIPR assay or high content high magnification optical microscopy, of 3D human cell spheroids, e.g., spheroids formed of mixed populations of neurons, oligodendrocytes, microglial cells, endothelial cells, or any combination thereof. In one embodiment, a multi-well optical assay is provided, such as a functional FLIPR assay, of 3D mixed population human cell spheroids in a multi-well format, e.g., a 96, 384 or 1536 microplate well, e.g., spheroids in a rounded bottom well format.

Further provided is an optical assay, e.g., a functional FLIPR assay, of 3D mixed population spheroids in which the spheroids in each microplate well are of uniform size, e.g., diameters that are +1-50 or +1-25 microns. In one embodiment, FLIPR generates real time functional data on 3D neuron based cell spheroids that are very consistent within a micro plate, e.g., well-to-well, and from plate to plate.

In one embodiment, the disclosure provides an optical assay including a functional FLIPR assay of 3D mixed population spheroids that respond to agonist or antagonist drug challenge in real time.

In one embodiment, the disclosure provides an optical assay, e.g., a functional FLIPR assay, of 3D mixed population spheroids derived from human primary cells, iPSc, differentiated cells, or other human cell lines.

Exemplary Therapeutic Methods and Compositions

The present disclosure provides methods to prevent or mitigate, e.g. inhibit or treat, in a human one or more symptoms associated with a disorder such as autism spectrum disorder or Rett syndrome. In some embodiments, methods are provided for inhibiting or treating neurological or developmental symptoms of a disease.

Methods are also provided for reducing the risk, progression or onset of a disease characterized by delayed growth, loss of normal movement and coordination, loss of communication abilities, abnormal hand and eye movements, breathing problems, cognitive disabilities, seizures, scoliosis, irregular heartbeat, or sleep disturbances.

Methods are further provided for reducing the risk, lessening the severity, or delaying the progression or onset of Rett disease.

In one embodiment, the composition to be administered comprises a 5-HT4 receptor selective agonist. In one embodiment, the composition to be administered comprises a zabicycloalkyl benzimidazolone. In one embodiment, the composition to be administered comprises a GABA receptor antagonist. In one embodiment, the composition to be administered comprises a benzodiazepine. In one embodiment, the composition to be administered comprises a competitive antagonist at the benzodiazepine receptor. In one embodiment, the composition to be administered comprises an acetazolamide.

In one embodiment, the composition to be administered comprises a selective noradrenaline reuptake inhibitor. In one embodiment, the composition to be administered comprises an antimuscarinic. In one embodiment, the composition to be administered comprises a selective serotonin receptor agonist. In one embodiment, the composition to be administered comprises a compound that enhances release of gonadotropin releasing hormone. In one embodiment, the composition to be administered comprises a selective serotonin reuptake inhibitor. In one embodiment, the composition to be administered comprises branched-chain saturated fatty acid anion. Tn one embodiment, the composition to be administered comprises an inhibitor of CYP2C9, glucuronyl transferase, histone deacetylase, or epoxide hydrolase. In one embodiment, the composition to be administered comprises a gamma-aminobutyric acid (GABA) agonist. In one embodiment, the composition to be administered comprises a locally-acting nonsteroidal anti-inflammatory drug (NSAID), e.g., with local anesthetic and analgesic properties. In one embodiment, the composition to be administered comprises a biindole, e.g., indirubin. In one embodiment, the composition to be administered comprises an anticholinergic agent. In one embodiment, the composition to be administered comprises a dopamine antagonist, e.g., with antiemetic or prokinetic properties. In one embodiment, the composition to be administered comprises a selective acetylcholinesterase inhibitor. In one embodiment, the composition to be administered comprises an antihistamine type. In one embodiment, the composition to be administered comprises a benzothiadiazine. In one embodiment, the composition to be administered comprises a positive allosteric modulator of glutamate AMPA receptors. In one embodiment. the composition to be administered comprises an anti-mimetic. In one embodiment, the composition to be administered comprises a selective serotonin inverse agonist. In one embodiment, the composition to be administered comprises an inhibitor of monoamine oxidase. In one embodiment, the composition to be administered comprises a reversible inhibitor of monoamine oxidase, e.g., selective, reversible inhibitor of monoamine oxidase A. In one embodiment, the composition to be administered comprises an alkaloid. In one embodiment, the composition comprises a vinca alkaloid.

In one embodiment, the composition comprises BIMU-8. In one embodiment, the composition comprises flumazenil. In one embodiment, the composition comprises acetazolamide. In one embodiment, the composition comprises N-methyl acetazolamide. In one embodiment, the composition comprises atomoxetine (tomoxetine). In one embodiment, the composition comprises benzhexol hydrochloride. In one embodiment, the composition comprises eletriptan. Tn one embodiment, the composition comprises iloperidone. In one embodiment, the composition comprises trazodone. In one embodiment, the composition comprises valproate. In one embodiment, the composition comprises baclofen. In one embodiment, the composition comprises benzydiamine hydrochloride. In one embodiment, the composition comprises bromoindirubin-3-oxime. In one embodiment, the composition comprises iperiden. In one embodiment, the composition comprises citalopram. In one embodiment, the composition comprises clebopride malate. In one embodiment, the composition comprises donepezil or an analog thereof, e.g., see Saghk et al. (Eur J Med Chem. 2016 Nov. 29;124:1026-1040. doi: 10.1016/j.ejmech.2016.10.042), the disclosure of which is incorporated by reference herein. Tn one embodiment, the composition comprises hydroxyzine dichloride. In one embodiment, the composition comprises IDRA-21. In one embodiment, the composition comprises ondansetron, dolastreon or palonosetron. In one embodiment, the composition comprises paroxetine. In one embodiment, the composition comprises pinmavanserin. In one embodiment, the composition comprises pirlindole mesylate. In one embodiment, the composition comprises selegiline hydrochloride. In one embodiment, the composition comprises vinpocetine.

Pharmaceutical Compositions

Pharmaceutical compositions having one or more of the compounds described herein, suitable for administration, e.g., nasal, parenteral or oral administration, such as by intravenous, intramuscular, topical or subcutaneous routes, or by any other route of administration that allows drug to be delivered to the body or specific organs and tissues of the body, such as intrathecal, intracerebroventricular or intraparenchymal delivery to the central nervous system, optionally further comprising sterile aqueous or non-aqueous solutions, suspensions, and emulsions. The compositions can further comprise auxiliary agents or excipients, as known in the art. The composition having one or more of the compounds described herein is generally presented in the form of individual doses (unit doses).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition having one or more of the compounds described herein is used for administration to an individual, it can further comprise salts. buffers, adjuvants, or other substances which are desirable for improving the efficacy of the composition.

In one embodiment, the pharmaceutical composition is part of a controlled release system, e.g., one having a pump, or formed of polymeric materials (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas. J. Macromol. Sci. Rev. Macromol. Chem., 23:61 (1983); see also Levy et al., Science 228:190 (1985); During et al., Ann. Neurol., 25:351 (1989); Howard et al., J. Neurosurg., 71:105 (1989)). Other controlled release systems are discussed in the review by Langer (Science, 249:1527 (1990)).

The pharmaceutical compositions having one or more of the compounds described herein comprise a therapeutically effective amount of compounds, for instance, those identified by the screening methods, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiaes for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective, together with a suitable amount of carrier so as to provide the form for proper administration to the patient. The formulation should suit the mode of administration.

The compositions may be systemically administered, e.g. orally, in combination with a pharmaceutically acceptable vehicle such as an inert diluent. For oral administration, the compound(s) may be combined with one or more excipients and used in the form of ingestible capsules, elixirs, suspensions, syrups, wafers, and the like. Such compositions should contain at least 0.1% of active compound. The percentage of the compositions and preparations may, of course, be varied and may conveniently be between about 2 to about 60% of the weight of a given unit dosage form. The amount of active compound in such useful compositions is such that an effective dosage level will be obtained.

The compositions may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. Various other materials may be present. For instance, a syrup or elixir may contain the compound, sucrose or fructose as a sweetening agent, methyl and propylparabens as preservatives, a dye and flavoring such as cherry or orange flavor. Of course, any material used in preparing any unit dosage form, including sustained-release preparations or devices, should be pharmaceutically acceptable and substantially non-toxic in the amounts employed.

The composition can also be delivered by intravenous, intraperitoneal, intra-arterial, intrathecal, intraparenchymal or intracerebroventicular infusion or injection, or any other route of administration where delivery of a liquid formulation is suitable or appropriate for drug delivery. Solutions of the compound(s) can be prepared in water or a suitable buffer, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of undesirable microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of undesirable microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Sterile injectable solutions are prepared by incorporating the compound(s) in the required amount in the appropriate solvent with various of the other ingredients enumerated above, as required, followed by irradiation, steam (heat) or filter sterilization or any other preparatory method that results in a formulation that is essentially free of bacterial and/or viral contamination. Useful liquid carriers include water, alcohols or glycols or water-alcohol/glycol blends, in which the present compound(s) can be dissolved or dispersed at effective levels, optionally with the aid of nontoxic surfactants.

Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the compositions can be determined by comparing their in vitro activity and in vivo activity in animal models.

Exemplary Embodiments

In one embodiment, a method to detect the effect of one or more
compounds on spheroids is provided. In one embodiment, the method includes contacting one or more spheroids of human cells of uniform diameter and one or more test compounds, wherein the spheroids are obtained from cells of an autism patient, cells of a Rett syndrome patient, or cells that are from a model of Rett syndrome. The effect of the one or more compounds on one or more of the spheroids is detected, e.g. measured, optionally relative to corresponding wild-type cells. In one embodiment, the one or more spheroids are in wells of a multi-well plate. In one embodiment, each well has one spheroid. In one embodiment, the wells are further contacted with a fluorescent molecule useful to detect calcium, and the amount or change in fluorescence over time is detected in one or more wells. In one embodiment, the amount or change in fluorescence is detecting a quantity of peaks of fluorescence, an amplitude of one or more of the peaks, peak spacing between one or more of the peaks, a width of one or more peaks, or any combination thereof. In one embodiment, the one or more spheroids comprise neurons. In one embodiment, the one or more spheroids comprise neurons and astrocytes. In one embodiment, the one or more spheroids comprise heart, liver, kidney, pancreas, lung, endothelial or epithelial cells.

In one embodiment, the one or more spheroids comprise microglial cells or oligodendrocytes. In one embodiment, the one or more spheroids comprise pericytes and endothelial cells. In one embodiment, the one or more spheroids comprise endothelial cells, microglial cells, neurons, oligodendrocytic cells, or any combination thereof. In one embodiment, the cells are progenitor cells. In one embodiment. the progenitor cells are progenitors of neurons, astrocytes, heart cells, liver cells, kidney cells, pancreas cells, lung cells, endothelial cells, or epithelial cells. In one embodiment, the one or more spheroids have a diameter of about 500 to about 600 microns. In one embodiment, the one or more spheroids have a diameter of about 450 to about 500 microns. In one embodiment, the one or more spheroids are cultured for at least 6 weeks before contacting with the one or more test compounds. In one embodiment, the fluorescent molecule comprises Calcium 3, Calcium 4, Calcium 5, Calcium 6, Fluo 3, or Fluo4. In one embodiment, the method further comprises contacting the wells with a cell membrane impermeant quencher. In one embodiment, the amount of change in fluorescence is compared to the fluorescence in a well with spheroids and the fluorescent molecule but no test compound.

In one embodiment, a method or prevent, inhibit or treat one or more symptoms of autism spectrum disorder in a human is provided. In one embodiment, a method or prevent, inhibit or treat one or more symptoms of Rett disease in a human is provided. The method includes, in one embodiment, administering to the human a composition comprising an effective amount of one or more of a 5-HT4 receptor selective agonist, a zabicycloalkyl benzimidazolone, a GABA receptor antagonist, a benzodiazepine, a competitive antagonist at the benzodiazepine receptor, an acetazolatnide, a selective noradrenaline reuptake inhibitor, an antimuscarinic, a selective serotonin receptor agonist, a compound that enhances release of gonadotropin releasing hormone, a selective serotonin reuptake inhibitor, a branched-chain saturated fatty acid anion, an inhibitor of CYP2C9, an inhibitor of glucuronyl transferase, an inhibitor of histone deacetylase, an inhibitor of epoxide hydrolase, a gamma-aminobutyric acid (GABA) agonist, a nonsteroidal anti-inflammatory drug (NSAID), a biindole, an anticholinergic, a dopamine antagonist, an acetylcholinesterase inhibitor, an antihistamine, a benzothiadiazine, a modulator of glutamate AMPA receptors, an anti-emetic, a serotonin inverse agonist, an inhibitor of monoamine oxidase, or an alkaloid. In one embodiment, the composition comprises acetazolamide, atomoxetine (tomoxetine), benzhexol hydrochloride, BIMU-8, eletriptan HBr salt, iloperidone, trazodone (Beneficat). valproate DPA, baclofen, benzydiarnine hydrochloride, bromoindirubin-3-oxime, biperiden, citalopram, clebopride malate, bonepezil, flumazenil, hydroxyzine dichloride, IDRA-21, ondansetron, paroxetine, pinmavanserin, pirlindole mesylate, selegiline hydrochloride, or vinpocetine. In one embodiment, the composition is orally administered. In one embodiment, the composition is a sustained release formulation. In one embodiment, the administration is intravenous, intra-arterial, subcutaneous, intranasal, intrathecal, intracerebroventricular, intraparenchymal, trans-retinal, intramuscular, transdermal, or rectal. In one embodiment, the composition is a sustained release formulation. In one embodiment, the amount inhibits or treats delayed growth, loss of normal movement, loss of coordination, loss of communication abilities, abnormal hand movements, abnormal eye movements, breathing problems, cognitive disabilities, seizures. scoliosis, irregular heartbeat, or sleep disturbances Also provided is a multi-well plate comprising one or more mixed human cell spheroids per well. In one embodiment, the spheroids are obtained from cells of an autism patient, cells of a Rett syndrome patient, or cells that are from a model of Rett syndrome. In one embodiment, the one or more spheroids comprise neurons and astrocytes. In one embodiment, the one or more spheroids comprise heart, liver, kidney, pancreas, lung, endothelial or epithelial cells. In one embodiment, the one or more spheroids comprise microglial cells or oligodendrocytes. In one embodiment, the one or more spheroids comprise pericytes and endothelial cells. In one embodiment, the one or more spheroids comprise endothelial cells, microglial cells, neurons, oligodendrocytic cells, or any combination thereof. Tn one embodiment, the one or more spheroids comprise progenitors of neurons, astrocytes, heart cells, liver cells, kidney cells, pancreas cells, lung cells, endothelial cells, or epithelial cells. In one embodiment, the wells comprise spheroids formed from different cells.

The above discussion is meant to be illustrative of the principle and various embodiments of the present invention. Numerous variations and modifications will become apparent to those skilled in the art such as using different cell types for example heart, liver, kidney, lung, skin, pancreas, spleen, bone in 3D spheroid form factors, once the above disclosure is fully appreciated. Tt is intended that the following claims be interpreted to embrace all such variations and modifications.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to detect the effect of one or more compounds on reversing or rescuing erratic calcium oscillation activity in spheroids, comprising:

contacting one or more spheroids of human cells of uniform diameter and one or more test compounds, wherein the spheroids are obtained from cells of an autism patient or cells of a Rett syndrome patient; and detecting the effect on reversing or rescuing erratic calcium oscillation activity of the one or more compounds on one or more of the spheroids.

2. The method of claim 1, wherein the one or more spheroids are in wells of a multi-well plate.

3. The method of claim 2, wherein each well has one spheroid.

4. The method of claim 2, wherein one or more wells are further contacted with a fluorescent molecule useful to detect calcium, and an amount or change in fluorescence over time is detected in the one or more wells.

5. The method of claim 4, wherein the amount or change in fluorescence is: a quantity of peaks of fluorescence, an amplitude of one or more of the peaks, peak spacing between one or more of the peaks, a width of one or more peaks, or any combination thereof.

6. The method of claim 1, wherein the one or more spheroids comprise neurons.

7. The method of claim 1, wherein the one or more spheroids comprise neurons and astrocytes.

8. The method of claim 1, wherein the human cells comprise heart cells, liver cells, kidney cells, pancreas cells, lung cells, brain cells, endothelial cells, or epithelial cells.

9. The method of claim 1, wherein the one or more spheroids comprise cells from a Rett disease patient.

10. The method of claim 1, wherein the one or more spheroids comprise microglial cells or oligodendrocytes.

11. The method of claim 1, wherein the one or more spheroids comprise pericytes and endothelial cells.

12. The method of claim 1, wherein the one or more spheroids comprise endothelial cells, microglial cells, neurons, oligodendrocytic cells, or any combination thereof.

13. The method of claim 1, wherein the cells are progenitor cells.

14. The method of claim 13, wherein the progenitor cells are progenitors of neurons, astrocytes, heart cells, liver cells, kidney cells, pancreas cells, lung cells, endothelial cells, or epithelial cells.

15. The method of claim 1, wherein the one or more spheroids have a diameter of about 500 to about 600 microns.

16. The method of claim 1, wherein the one or more spheroids have a diameter of about 450 to about 500 microns.

17. The method of claim 1, wherein the one or more spheroids are cultured for at least 4 to 6 weeks before contacting with the one or more test compounds.

18. The method of claim 4 wherein the fluorescent molecule comprises Calcium 3, Calcium 4, Calcium 5, Calcium 6, Fluo 3, or Fluo4.

19. The method of claim 3, further comprising contacting the wells with a cell membrane impermeant quencher.

20. The method of claim 4, wherein the amount of change in fluorescence is compared to the fluorescence in a well with spheroids and the fluorescent molecule but no test compound.

* * * * *